United States Patent [19]
Godfrey

[11] Patent Number: 5,993,210
[45] Date of Patent: Nov. 30, 1999

[54] DENTIST'S TOOTH SEPARATOR

[76] Inventor: Duane Kent Godfrey, 3255 Western Ave., Idaho Falls, Id. 83406

[21] Appl. No.: 09/188,862

[22] Filed: Nov. 9, 1998

[51] Int. Cl.⁶ ........................................................ A61C 3/14
[52] U.S. Cl. .............................................. 433/159; 433/149
[58] Field of Search ................................. 433/159, 149, 433/4

[56] References Cited

U.S. PATENT DOCUMENTS

| | | | |
|---|---|---|---|
| 388,619 | 8/1888 | Booth | 433/159 |
| 545,754 | 9/1895 | Wishart | 433/148 |
| 600,257 | 3/1898 | Capwell | 433/149 |
| 777,821 | 12/1904 | Walker | 433/149 |
| 791,859 | 6/1905 | Barnes | 433/149 |
| 1,349,767 | 8/1920 | Ivory | 433/159 |
| 3,713,222 | 1/1973 | Tofflemire | 433/159 |

FOREIGN PATENT DOCUMENTS

| | | | |
|---|---|---|---|
| 3436147 | 4/1986 | Germany | 433/159 |

*Primary Examiner*—John J. Wilson
*Attorney, Agent, or Firm*—Hopkins Roden Crockett Hansen & Hoopes, PLLC

[57] ABSTRACT

A scissor-like device having narrow jaws and a ratchet tooth closing clamp between the two handle halves that operates like a hemostat, i.e. it maintains the jaws in a fixed position. The jaws are either curved or wedge-shaped to pry the teeth slightly apart during the filling procedure. In a first embodiment closing the handle separates two teeth from a center tooth. In a second embodiment closing the handles separates two adjacent teeth.

1 Claim, 3 Drawing Sheets

DENTIST'S TOOTH SEPARATOR

TECHNICAL FIELD

This invention relates in general to a device that can be used to separate teeth during a dental tooth filling procedure.

BACKGROUND OF THE INVENTION

In dental filling procedures for molars and premolars, a metal matrix band is placed around the tooth to be worked on. It is desirable to slightly separate the one or two adjacent teeth (one in front and one behind) depending on the size of the filling. If the filling is on a forward portion of the tooth, only the forward adjacent tooth needs to be separated from the matrix banded tooth. If the filling goes from front to back of the tooth, both adjacent teeth need to be slightly separated from the affected tooth.

The reason for the separation is to allow the adjacent teeth to move towards the filled tooth after the filling is completed to close up the gap. This prevents food particles from being lodged in the space between the filled tooth and adjacent teeth.

Tooth separator devices have been in use that include movable wedge shapes, threaded clamps, wedges and other mechanical devices.

It is the purpose of this invention to provide an adjustable tooth separator that maintains a fixed separation between one or more teeth.

SUMMARY OF THE INVENTION

A scissor-like device having narrow jaws and a ratchet tooth closing clamp between the two handle halves that operates like a hemostat, i.e. it maintains the jaws in a fixed position. The jaws are either curved or wedge-shaped to pry the teeth slightly apart during the filling procedure.

Specifically, the dentist's tooth separator consists of a pair of arcuate jaws; a pair of handle halves attaching to the jaws; a center pivot pin connecting the pair of handle halves; and a ratchet tooth clamp wherein when the handle halves are in a closed position, the ratchet tooth clamp maintains a fixed position of the arcuate jaws.

DETAILED DESCRIPTION OF THE INVENTION

Figure 1:
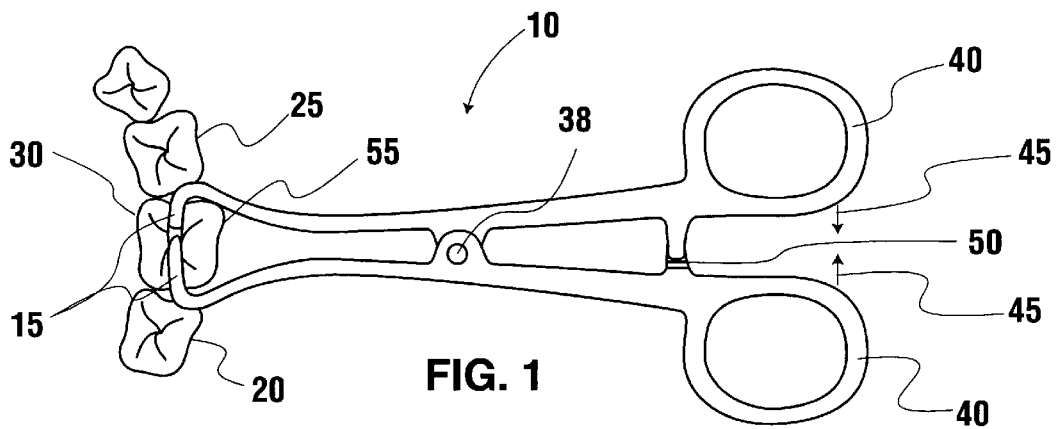
FIG. 1 is a top view of the tooth separator.
Figure 2:
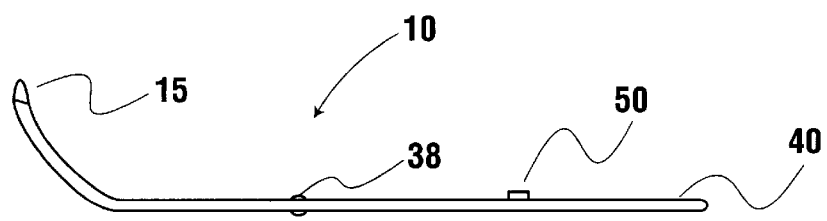
FIG. 2 is a side elevation of the tooth separator.

The first embodiment illustrates in FIGS. 1 through 4 a tooth separator 10 having a pair of pointed and arcuate jaws 15 that can separate two adjacent teeth 20, 25 from the center tooth 30. The jaws 15 are moved in direction arrow 35 by squeezing handle halves 40 in direction 45. This causes the jaws 15 to separate since the handle halves 40 are attached by pivot pin 38. When the proper tooth separation is obtained, the ratchet tooth clamp 50 between the handle halves 40 maintain the jaws in a fixed position and the handle halves 40 can be released. The jaws 15 actually are not bearing on the tooth 30 which has a metal matrix band 55 surrounding the tooth. The matrix band 55 acts as a cofferdam to confine the dental filling material. Note that in this embodiment the jaws are inserted from above the tooth.

Figure 5:
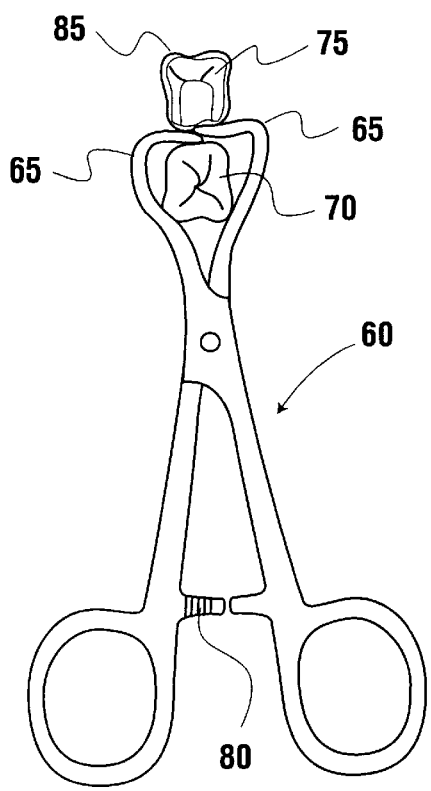
FIGS. 5 and 6 are top views of a second embodiment of the tooth separator.
Figure 6:
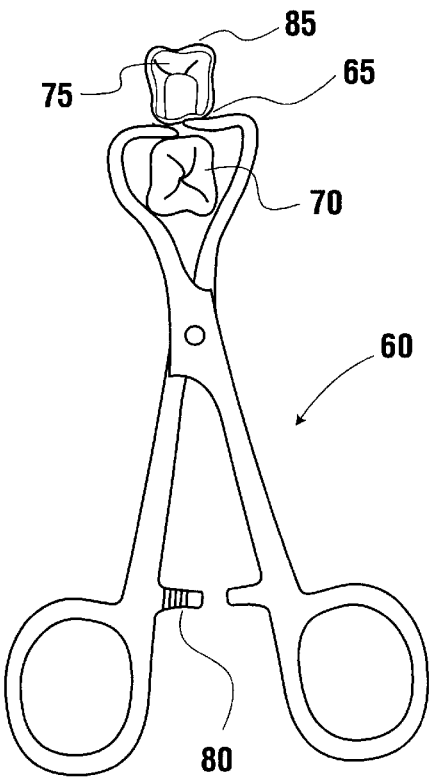
Figure 7:
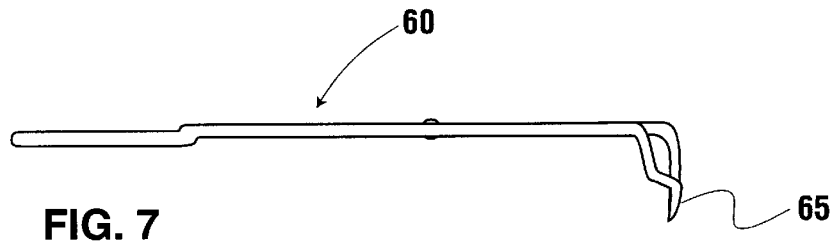
FIGS. 7 and 8 are side elevations of the tooth separator.
Figure 8:
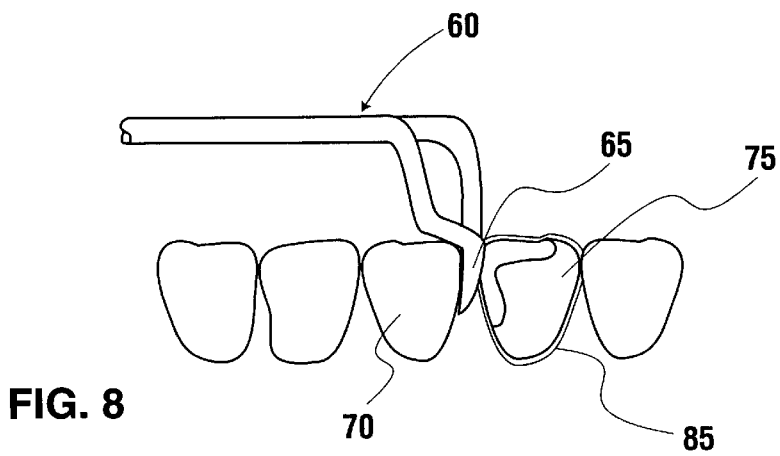

A second embodiment is illustrated in FIGS. 5 through 8. In this tooth separator 60 the thin, flat arcuate jaws 65 slide between two adjacent teeth 70 and 75. FIG. 6 illustrates the jaws 65 position at first contact with the adjacent teeth 70 and 75. FIG. 5 illustrates the jaws 65 in the fully closed position. The fully closed position is maintained by ratchet tooth clamp 80. As in the prior embodiment of FIGS. 1 through 4, the arcuate jaws bear against the tooth 70 and matrix band 85. As can be seen, this instrument separates only one tooth from another.

Figure 9:
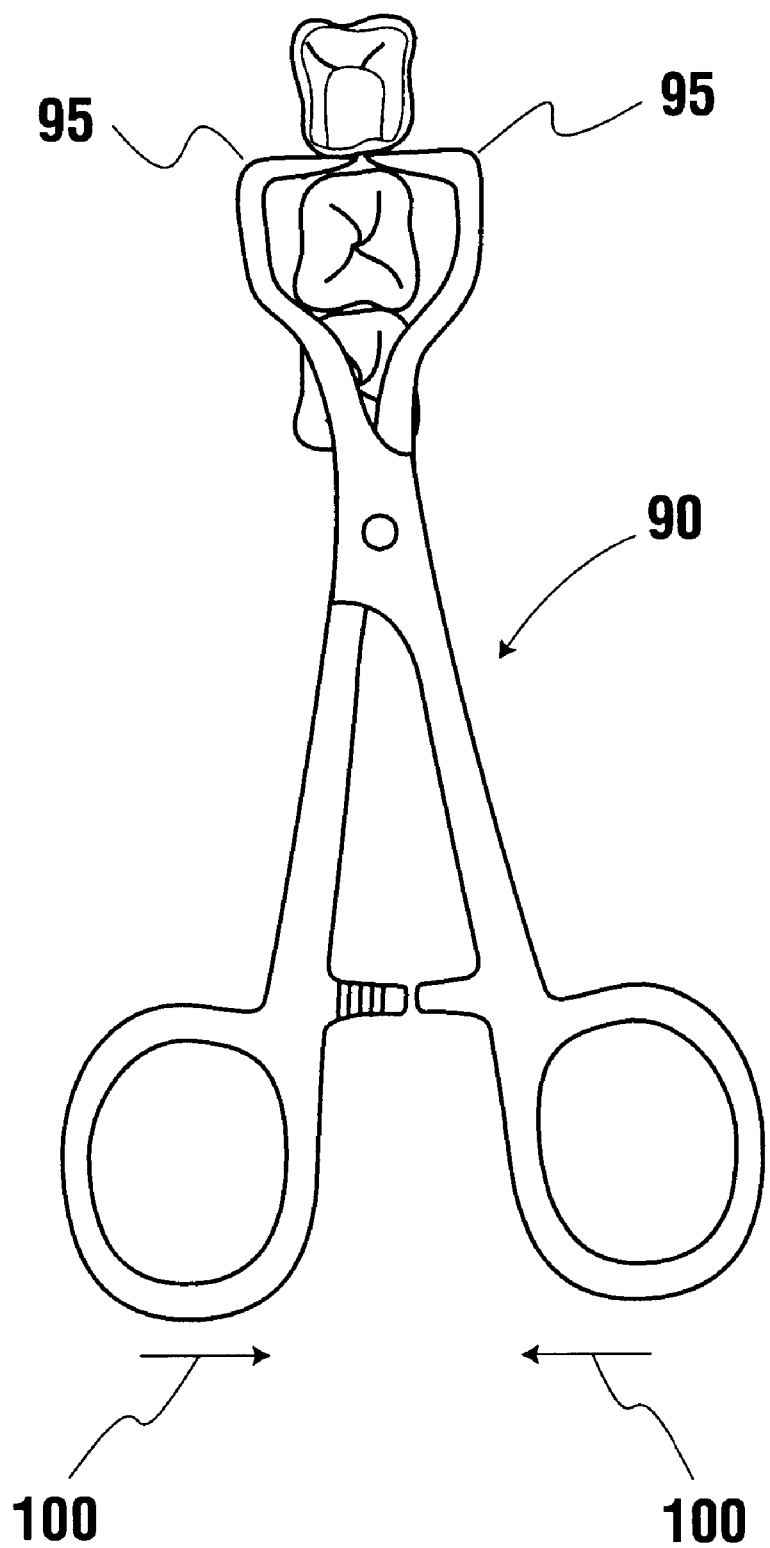
FIG. 9 is a top view of a third embodiment of the tooth separator.

FIG. 9 is a third embodiment showing another tooth separator 90 having pointed jaws 95 that separate adjacent teeth when the handle is moved in direction 100.

While the present invention has been described by reference to specific embodiments, it will be apparent that other alternative embodiments and methods of implementation or modification may be employed without departing from the true spirit and scope of the invention.

What is claimed is:

1. A dentist's tooth separator comprising
    a) a pair of pointed arcuate jaws;
    b) a pair of handle halves having an open and closed position, said handle halves attaching to the jaws;
    c) a center pivot pin connecting the pair of handle halves; and
    d) a ratchet tooth clamp wherein when the handle halves are in a closed position, the ratchet tooth clamp maintains a fixed position of the arcuate jaws, wherein the closed position of the handle halves separates the arcuate jaws thereby separating a pair of adjacent teeth from a center tooth.

* * * * *

UNITED STATES PATENT AND TRADEMARK OFFICE
CERTIFICATE OF CORRECTION

PATENT : 5,993,210

DATED : 11/30//99

INVENTOR(S): Duane Kent Godfrey

It is certified that error appears in the above-identified patent and that said Letters Patent is hereby corrected as shown below:

The title page should be deleted to be replaced with the attached title page.

Signed and Sealed this

Twenty-fourth Day of October, 2000

Attest:

Q. TODD DICKINSON

*Attesting Officer*   *Director of Patents and Trademarks*

United States Patent
Godfrey

Patent Number: 5,993,210
Date of Patent: Nov. 30, 1999

[54] DENTIST'S TOOTH SEPARATOR

[76] Inventor: Duane Kent Godfrey, 3255 Western Ave., Idaho Falls, Id. 83406

[21] Appl. No.: 09/188,862

[22] Filed: Nov. 9, 1998

[51] Int. Cl.⁶ .................................................. A61C 3/14
[52] U.S. Cl. ........................................ 433/159; 433/149
[58] Field of Search ............................... 433/159, 149, 433/4

[56] References Cited

U.S. PATENT DOCUMENTS

| 388,619 | 8/1888 | Booth | 433/159 |
|---|---|---|---|
| 545,754 | 9/1895 | Wishart | 433/148 |
| 600,257 | 3/1898 | Capwell | 433/149 |
| 777,821 | 12/1904 | Walker | 433/149 |
| 791,859 | 6/1905 | Barnes | 433/149 |
| 1,349,767 | 8/1920 | Ivory | 433/159 |
| 3,713,222 | 1/1973 | Tofflemire | 433/159 |

FOREIGN PATENT DOCUMENTS 3436147  4/1986  Germany ................ 433/159

Primary Examiner—John J. Wilson
Attorney, Agent, or Firm—Hopkins Roden Crockett Hansen & Hoopes, PLLC

[57] ABSTRACT

A scissor-like device having narrow jaws and a ratchet tooth closing clamp between the two handle halves that operates like a hemostat, i.e. it maintains the jaws in a fixed position. The jaws are either curved or wedge-shaped to pry the teeth slightly apart during the filling procedure. In a first embodiment closing the handle separates two teeth from a center tooth. In a second embodiment closing the handles separates two adjacent teeth.

1 Claim, 3 Drawing Sheets

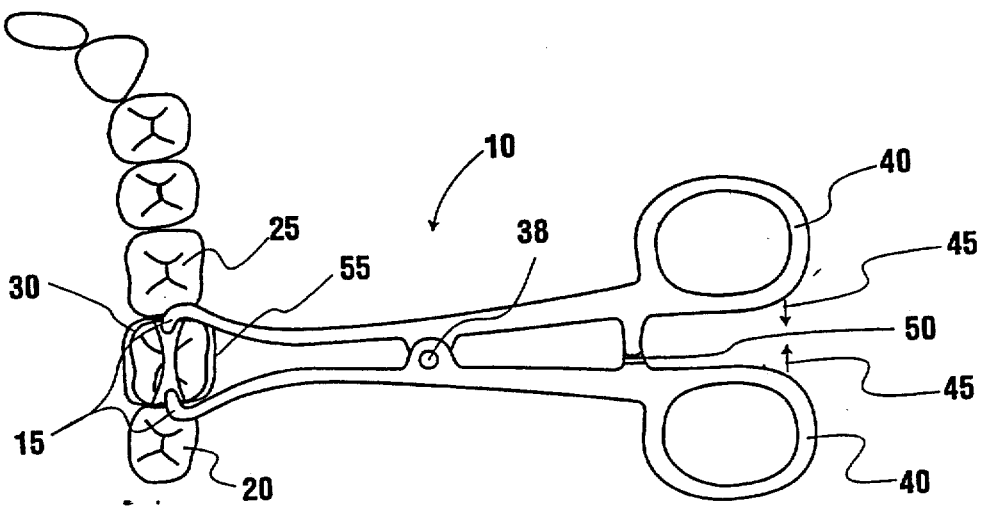

UNITED STATES PATENT AND TRADEMARK OFFICE
CERTIFICATE OF CORRECTION

Page 3 of 4

PATENT NO. : 5,993,210
DATED : 11/30/99
INVENTOR(S) : Duane Kent Godfrey

It is certified that error appears in the above-identified patent and that said Letters Patent is hereby corrected as shown below:

On the drawing sheet 1 replace the figure 1 with the following figure 1:

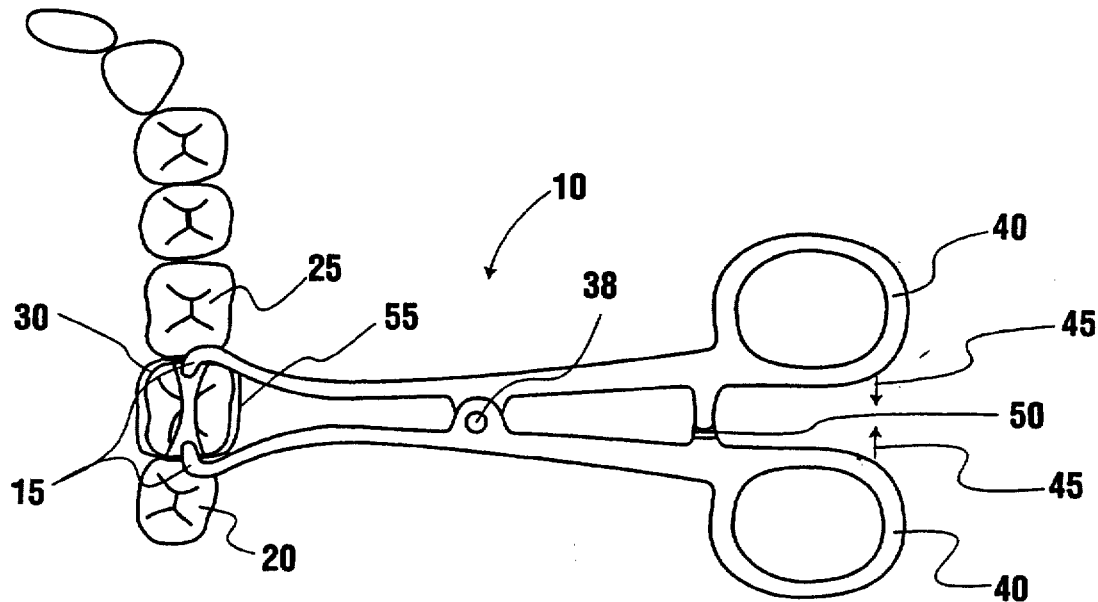

UNITED STATES PATENT AND TRADEMARK OFFICE
CERTIFICATE OF CORRECTION

Page 4 of 4

PATENT NO. : 5,993,210
DATED : 11/30/99
INVENTOR(S) : Duane Kent Godfrey

Figures 3, 4:
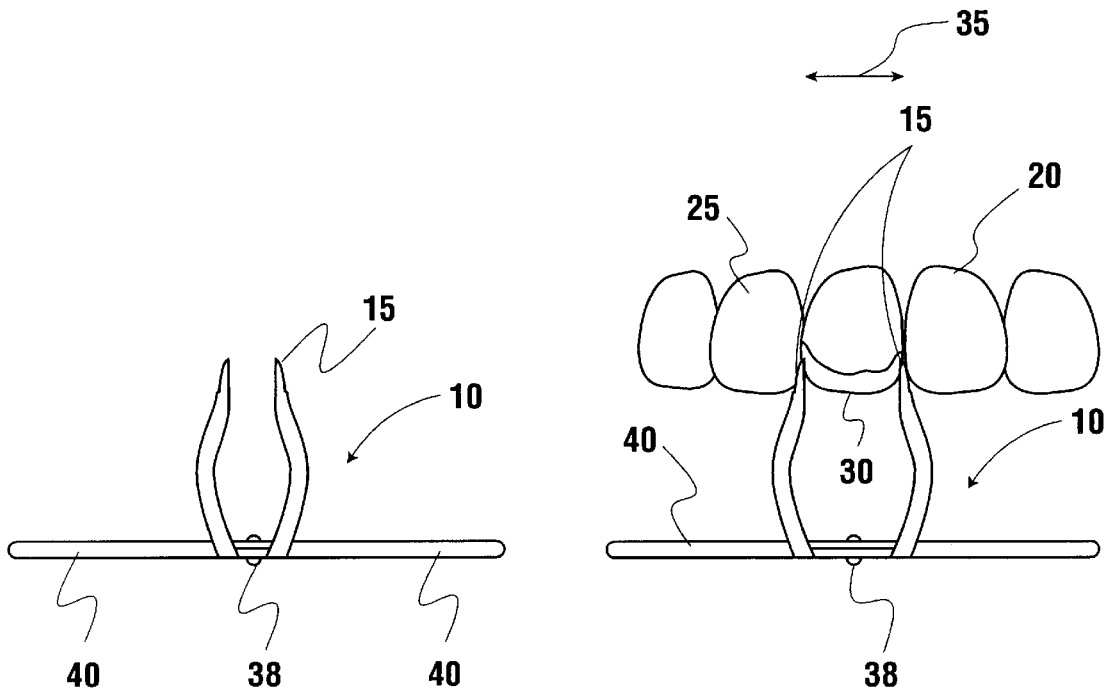
FIG. 3 is a front elevation of the tooth separator.
FIG. 4 is a front elevation of the tooth separator inserted between two teeth adjacent to the affected tooth.

It is certified that error appears in the above-identified patent and that said Letters Patent is hereby corrected as shown below:

On the drawing sheet 1 replace the figure 4 with the following figure 4:

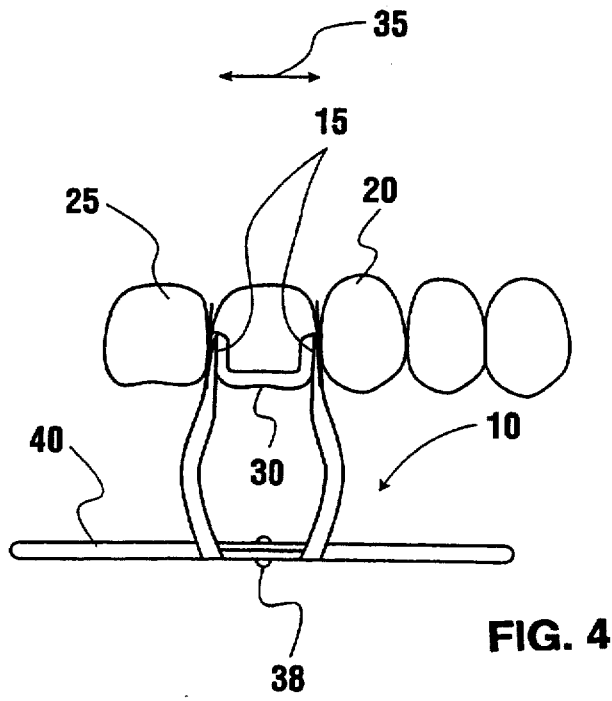

FIG. 4